United States Patent
Bankers et al.

(10) Patent No.: US 8,133,434 B2
(45) Date of Patent: Mar. 13, 2012

(54) AIR TREATMENT DEVICE UTILIZING A SENSOR FOR ACTIVATION AND OPERATION

(75) Inventors: Jeffrey Bankers, Phoenix, AZ (US); Sanam Nassirpour, Phoenix, AZ (US); Kevin Hafer, Chandler, AZ (US)

(73) Assignee: The Dial Corporation, Scottsdale, AZ (US)

(*) Notice: Subject to any disclaimer, the term of this patent is extended or adjusted under 35 U.S.C. 154(b) by 554 days.

(21) Appl. No.: 12/355,041

(22) Filed: Jan. 16, 2009

(65) Prior Publication Data

US 2009/0185952 A1 Jul. 23, 2009

Related U.S. Application Data

(60) Provisional application No. 61/021,807, filed on Jan. 17, 2008.

(51) Int. Cl.
| | |
|---|---|
| *A61L 9/00* | (2006.01) |
| *A62B 7/08* | (2006.01) |
| *B01D 47/00* | (2006.01) |
| *G07F 11/00* | (2006.01) |
| *A24F 15/04* | (2006.01) |
| *A24F 25/00* | (2006.01) |
| *B65H 1/00* | (2006.01) |
| *B67D 5/08* | (2006.01) |
| *B67D 3/00* | (2006.01) |
| *A01G 27/00* | (2006.01) |
| *B05B 7/00* | (2006.01) |

(52) U.S. Cl. ....... 422/3; 422/1; 422/5; 422/28; 422/108; 422/119; 422/120; 422/123; 422/306; 261/75; 261/DIG. 17; 261/DIG. 67; 261/DIG. 88; 261/DIG. 89; 221/1; 221/9; 221/186; 221/197; 221/303; 239/1; 239/34; 239/704; 239/71; 239/145; 239/302; 222/52; 222/187; 222/630

(58) Field of Classification Search .................. 422/1, 3, 422/5, 28, 108, 119–120, 123, 306; 261/75, 261/DIG. 17, DIG. 67, DIG. 88, DIG. 89; 221/1, 9, 186, 197, 303; 239/1, 34, 704, 239/71, 145, 302; 222/52, 187, 630
See application file for complete search history.

(56) References Cited

U.S. PATENT DOCUMENTS

| | | | | |
|---|---|---|---|---|
| 7,547,420 | B2* | 6/2009 | Schroder | 422/186.04 |
| 2005/0077376 | A1* | 4/2005 | Hess et al. | 239/34 |
| 2006/0076366 | A1* | 4/2006 | Furner et al. | 222/402.13 |

* cited by examiner

*Primary Examiner* — Jill Warden
*Assistant Examiner* — Monzer Chorbaji
(74) *Attorney, Agent, or Firm* — Thomas G. Krivulka

(57) ABSTRACT

In an exemplary embodiment, the present invention includes at least one reservoir with a delivery mechanism in communication therewith. The delivery mechanism draws an air treatment material from the reservoir and provides the air treatment material in response to a decreased level of active air treatment material or the detection of a malodor. Additionally, the delivery mechanism includes a control system and a detection system. The control system activates the detection system at a timed interval or in response to a change in one or more ambient conditions (e.g., motion, temperature, light, humidity, etc.). Once activated, the detection system samples the environment for either the level of active air treatment material or the quality of the environment.

3 Claims, 5 Drawing Sheets

AIR TREATMENT DEVICE UTILIZING A SENSOR FOR ACTIVATION AND OPERATION

CROSS-REFERENCE TO RELATED APPLICATION

This Non-Provisional patent application claims the benefit of U.S. Provisional Patent Application Ser. No. 61/021,807, entitled AIR TREATMENT DEVICE UTILIZING A SENSOR FOR ACTIVATION AND OPERATION and filed Jan. 17, 2008, which is incorporated by reference herein in its entirety.

FIELD OF INVENTION

The present invention generally relates to air treatment devices and more particularly to air fresheners having a control mechanism that activates a delivery mechanism, the delivery mechanism being capable of treatment in response to detection of a malodor.

BACKGROUND OF THE INVENTION

Conventional vapor-dispensing products include a volatizable material and a transport system configured to facilitate evaporation of the volatizable material into the surrounding air. Such volatizable materials include fragrances, air fresheners, deodorizers, odor eliminators, odor counteractants, insecticides, insect repellants, medicinal substances, disinfectants, sanitizers, mood enhancers, and aroma therapy compositions, scented water, oil, alcohol, gel, solids or membrane type air treatment material. Air fresheners are common exemplary vapor-dispensing devices and are often classified as continuous release fresheners or burst fresheners.

Continuous release fresheners, active or passive, provide substantially constant air treatment material intensity over extended periods of time and typically include a reservoir and a wick or some other air treatment material pathway.

Burst fresheners are typically designed to provide instantaneous dispersions, for example, to combat transient or elevated malodor levels, and lack the prolonged effect provided by continuous release systems. Conventional burst systems employ aerosol propellants or mechanical type pumps and spray nozzles to create dispersions that typically dissipate quickly in the air. Burst systems may be initiated by the user or set to dispense air treatment material at specific time intervals. Burst systems provide an instantaneous increase in air treatment material intensity.

Recent burst systems have incorporated detection mechanisms that provide a burst in response to the detection of a malodor. However, the detection mechanisms used in these burst systems require significant power in order to continuously operate. As such, the batteries that power the detection mechanisms are prematurely drained. Thus, a burst system where the detection mechanism is active part-time would be particularly beneficial in that the useful life of the battery would be prolonged.

In short, there is no available product providing a burst release wherein the burst is in response to the detection of a malodor and wherein the detection mechanism is only active at specific time intervals or in response to a change in one or more ambient conditions. Thus, there is a need for a vapor-dispensing device that overcomes these and other limitations of the prior art.

SUMMARY OF THE INVENTION

In an exemplary embodiment, the present invention includes at least one reservoir with a delivery mechanism in communication therewith. The delivery mechanism draws an air treatment material from the reservoir. The delivery mechanism provides the air treatment material in response to a decreased level of active air treatment material or the detection of a malodor.

Additionally, the delivery mechanism includes a control system and a detection system. The control system regulates the activity of the detection system, thereby allowing for periods of inactivity of the detection system for energy conservation. In other words, the control system activates the detection system of the delivery mechanism at a timed interval or in response to a change in one or more ambient conditions (e.g., motion, temperature, light, humidity, etc.). Once activated, the detection system samples the environment for either the level of active air treatment material or the quality of the environment.

BRIEF DESCRIPTION OF THE DRAWINGS

These and other features, aspects and advantages of the present invention will become better understood with reference to the following description, appending claims, and accompanying drawings where:

DETAILED DESCRIPTION

The following descriptions are of exemplary embodiments of the invention only, and are not intended to limit the scope or applicability of the invention in any way. Rather, the following description is intended to provide convenient illustrations for implementing various embodiments of the invention. As will become apparent, various changes may be made without departing from the spirit or scope of the invention as set forth in the appended claims.

For the sake of brevity, functional embodiments of the apparatus and systems (and components of the individual operating components of the systems) may not be described in detail herein. Furthermore, the connecting lines shown in the various figures contained herein are intended to represent exemplary functional relationships or physical connections between the various elements. It should be noted that many alternative or additional functional relationships or physical connections may be present in a practical system.

As used herein, air treatment material may comprise one or more of volatizable materials, fragrances, air fresheners, deodorizers, odor eliminators, odor counteractants, insecticides, insect repellants, medicinal substances, disinfectants, sanitizers, mood enhancers, and aroma therapy compositions, scented water, oil, alcohol, gel, solids or membrane type air treatment material.

In an exemplary embodiment, the present invention includes at least one reservoir with a delivery mechanism in communication therewith. The delivery mechanism draws an air treatment material from the reservoir. The delivery mechanism provides the air treatment material in response to a decreased level of active air treatment material or the detection of a malodor.

Additionally, the delivery mechanism includes a control system and a detection system. The control system regulates the activity of the detection system, thereby allowing for periods of inactivity of the detection system for energy conservation. In other words, the control system activates the detection system of the delivery mechanism at a timed interval or in response to a change in one or more ambient conditions (e.g., motion, temperature, light, humidity, etc.). Thus, the control system allows the detection system to remain inactive when not in use. Once activated, the detection system samples the environment for either the level of active air treatment material or the quality of the environment.

Figure 1:
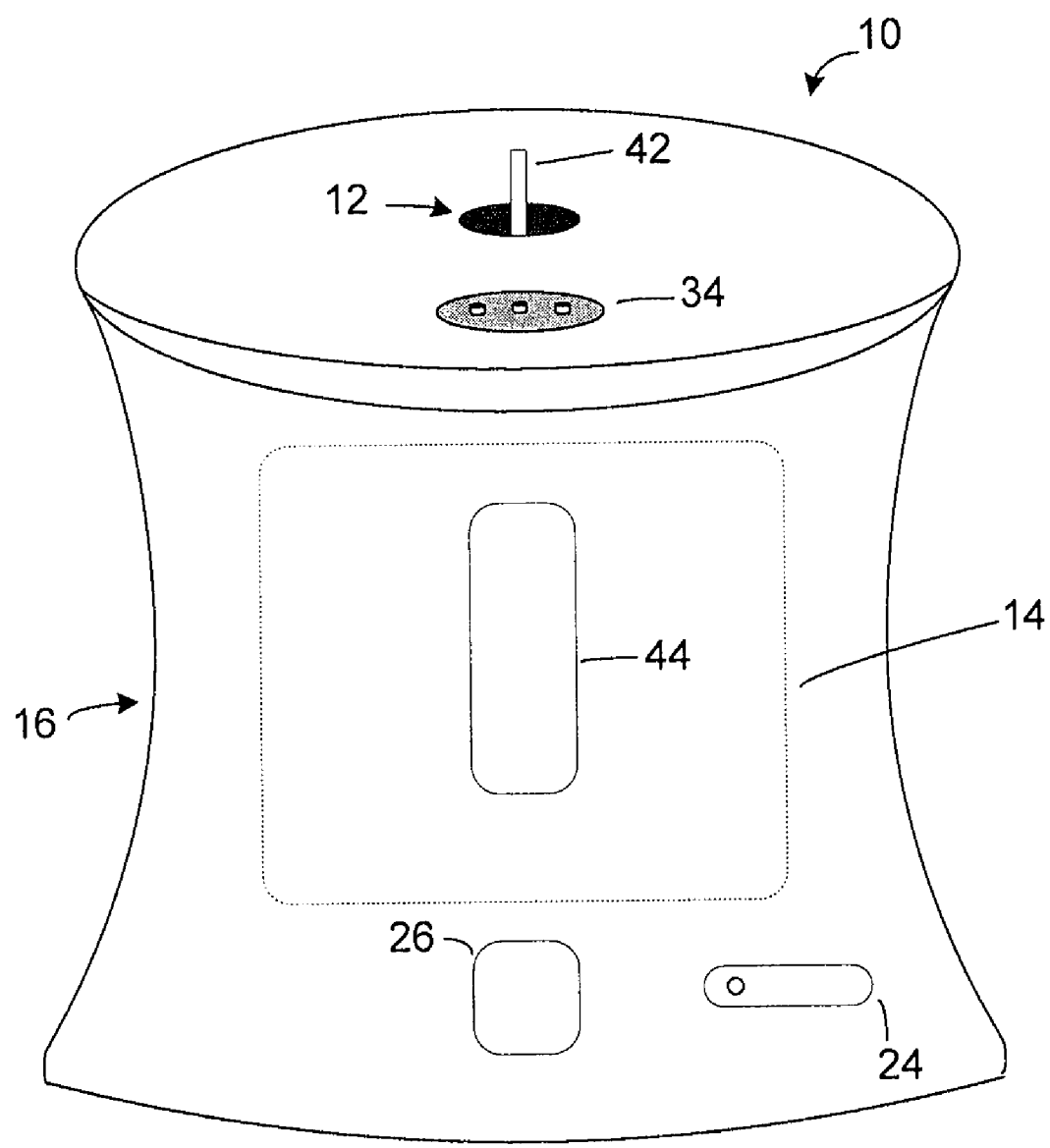
FIG. 1 shows a view of an air treatment device.

Referring now to FIG. 1, an exemplary air treatment device 10 in accordance with the present invention is shown. The air treatment device 10 includes a delivery mechanism 12 that draws an air treatment material from a reservoir 14 which is received in a housing 16. Dispersion of the air treatment material from the reservoir 14 via a conduit 42 can be by any mechanism known by one of ordinary skill in the art. Some examples include but are not limited to aerosol propellants, mechanical type pumps and spray nozzles, or any other propellant mechanisms.

As shown in block diagrams in FIGS. 2 and 3, the delivery mechanism 12 includes a control system 20 and a detection system 22. In exemplary embodiments, the control system 20 regulates the activity of the detection system 22.

Control System

In an exemplary embodiment, as shown in FIGS. 1 and 2, the control system 20 includes one or more of a selection mechanism 24, an ambient sensor 26, and a timing control circuit 28. The timing control circuit 28 communicates with the detection system 22 to regulate the activity of the detection system 22.

In an exemplary embodiment, the operation of the control system 20 depends on the user's choice. For example, in certain instances a user may wish to have the ambient sensor 26 activate the detection system 22, while in other instances a user may wish to have timed activation of the detection system 22. Still further, a user may wish to have both ambient sensor activation and timed activation. Still further, a user may wish to manually activate the detection system 22. The selection mechanism 24 operates to indicate in what mode the air treatment device 10 will operate. The selection mechanism 24 may be a switch or any other suitable mechanism that allows the user to choose the mode in which the air treatment device 10 will operate.

With ambient sensor activation, in an exemplary embodiment, the ambient sensor 26 monitors the environment for changes in or the presence or absence of one or more ambient conditions (e.g., motion, temperature, light, humidity, etc.). It should be understood by one of ordinary skill in the art that any suitable ambient sensor exhibiting the qualities discussed herein may be used.

In an exemplary embodiment, the sensitivity of the ambient sensor 26 may be adjusted by the selection mechanism 24. In another exemplary embodiment, the sensitivity of the ambient sensor 26 is set from a factory.

If a change occurs, an indication signal 27 is sent to the timing control circuit 28. The timing control circuit 28 then activates the detection system 22 at specific time intervals and/or for a specific duration. In an exemplary embodiment, the time intervals of the timing control circuit 28 may be adjusted by the selection mechanism 24. In another exemplary embodiment, the time intervals of the timing control circuit 28 are set from a factory.

In an exemplary embodiment, as shown in FIG. 2, the timing control circuit 28 and the ambient sensor 26 are interconnected by a feedback circuit 30 such that the timing control circuit 28 controls the ambient sensor 26.

With timed activation, the detection system 22 is activated by the timing control circuit 28 at specific time intervals and/or for a specific duration without regard to any changes in or the presence or absence of one or more ambient conditions.

In an exemplary embodiment, the time intervals of the timing control circuit 28 may be adjusted by the selection mechanism 24. In another exemplary embodiment, the time intervals of the timing control circuit 28 are set from a factory.

Once activated, the detection system samples the environment for either the level of active air treatment material or the quality of the environment, as discussed below.

Detection System

Turning now to FIGS. 1 and 3, in an exemplary embodiment, the detection system 22 includes one or more of an intensity selector 32, a sensor 34, an activation circuit 36, and a delivery system 38.

In an exemplary embodiment, the sensor 34 is configured to sample the environment for either the level of active air treatment material or the quality of the environment. When the sensor 34 detects either a decreased level of active air treatment material or the presence of a malodor, an indication signal 37 is sent to the activation circuit 36. In an exemplary embodiment, the sensor 34 is capable of detecting and/or distinguishing between a plurality of malodors such that a single air treatment device 10 may be used in multiple locations. In an exemplary embodiment, the sensor 34 is a metal oxide sensor, however, it should be understood by one of ordinary skill in the art that any suitable sensor exhibiting the qualities discussed herein may be used.

In an exemplary embodiment, upon receiving the indication signal 37 from the sensor 34, the activation circuit 36 activates the delivery system 38 thereby causing it to dispense the air treatment at specific time intervals and/or for a specific duration.

In an exemplary embodiment, as shown in FIG. 3, the activation circuit 36 and the sensor 34 are interconnected by a feedback circuit 40 such that the activation circuit 36 controls the sensor 34. In accordance with one aspect of an exemplary embodiment, the activation circuit 36 disengages the sensor 34 for an operational time period via the feedback circuit 40 if the activation circuit 36 triggers the dispersion of the air treatment material.

In accordance with one aspect of an exemplary embodiment, the interconnection of the activation circuit 36 and the sensor 34 by the feedback circuit 40 provides for additional power conservation. Specifically, because the sensor 34 may need to be heated to a high temperature to work, there is power conservation if the activation circuit 36 also controls the sensor 34. For example, the activation circuit 36 can turn off the sensor 34 when it is not in use.

In an exemplary embodiment, as shown in FIG. 3, the responsiveness of the detection system 22 is adjustable. For example, the responsiveness of the detection system 22 may be adjusted to high, medium, low, or off via the intensity selector 32, depending on the user's wants or needs.

Dispersion of the air treatment material by the delivery system 38 can be by any mechanism known by one of ordinary skill in the art. Some examples include but are not limited to aerosol propellants, mechanical type pumps and spray nozzles, or any other propellant mechanisms. To be clear, the delivery system 38 is not meant to be limiting and may comprise an atomizer, spritzer, sprayer, pump, nozzle, or any other suitable dispenser. In other words, it should be understood by one of ordinary skill in the art that any delivery system now known or as yet unknown in the art can suitably be configured to be used in the present invention.

Figure 3:
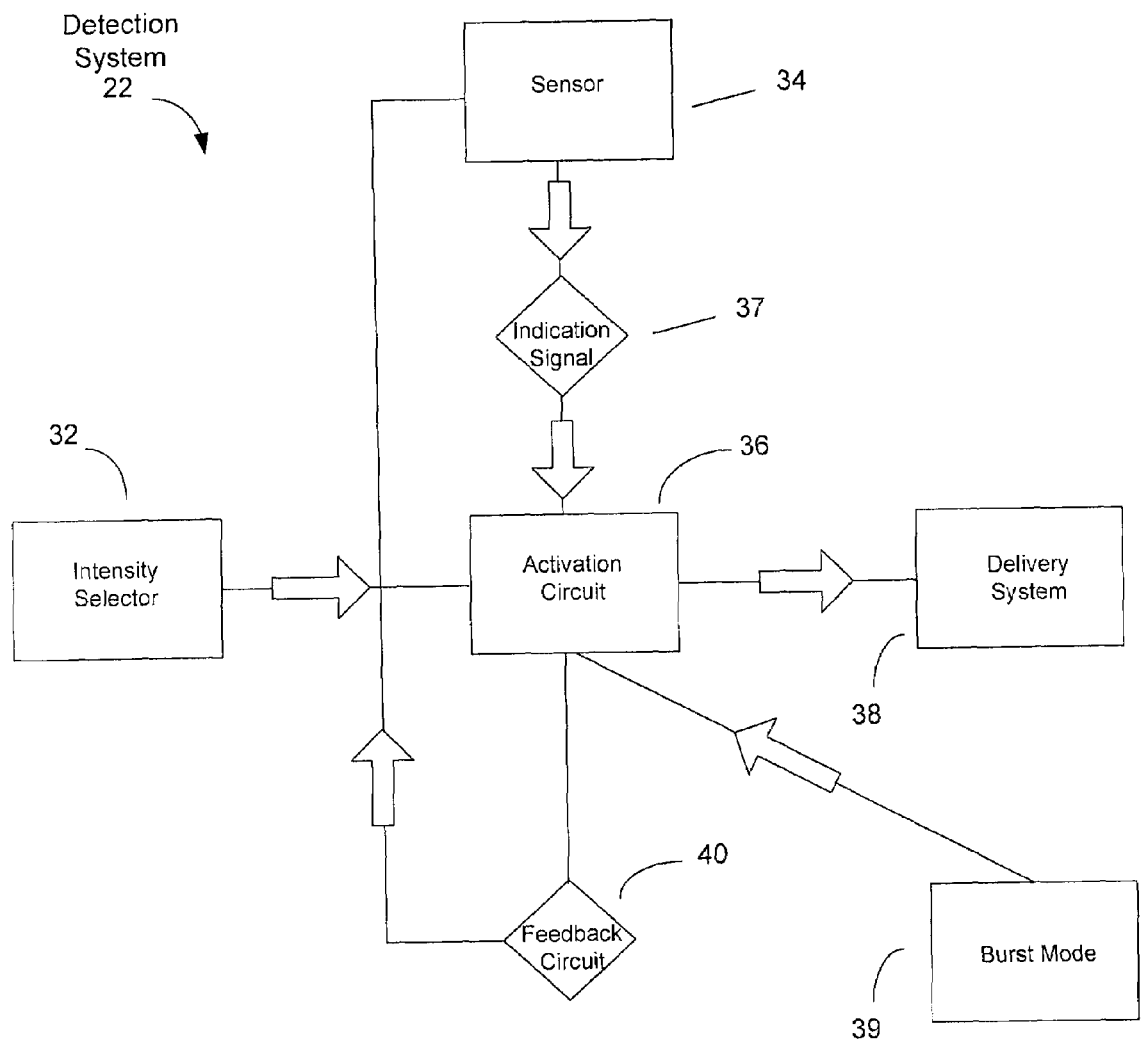
FIG. 3 shows a block diagram of a detection system and method of use of the air treatment device.

In an exemplary embodiment, as shown in FIG. 3, the detection system 22 comprises a burst mode 39 that may be initiated by an actuator 44 (shown in FIG. 1) on the air treatment device 10 to immediately dispense the air treatment or to dispense the air treatment at specific time intervals and/or for a specific duration. The user, by pressing the actuator 44 activates the burst mode 39. In an exemplary embodiment, upon being triggered by the burst mode 39, the activation circuit 36 activates the delivery system 38 thereby causing it to dispense the air treatment at specific time intervals and/or for a specific duration.

Operation Of Delivery Mechanism

Figure 2:
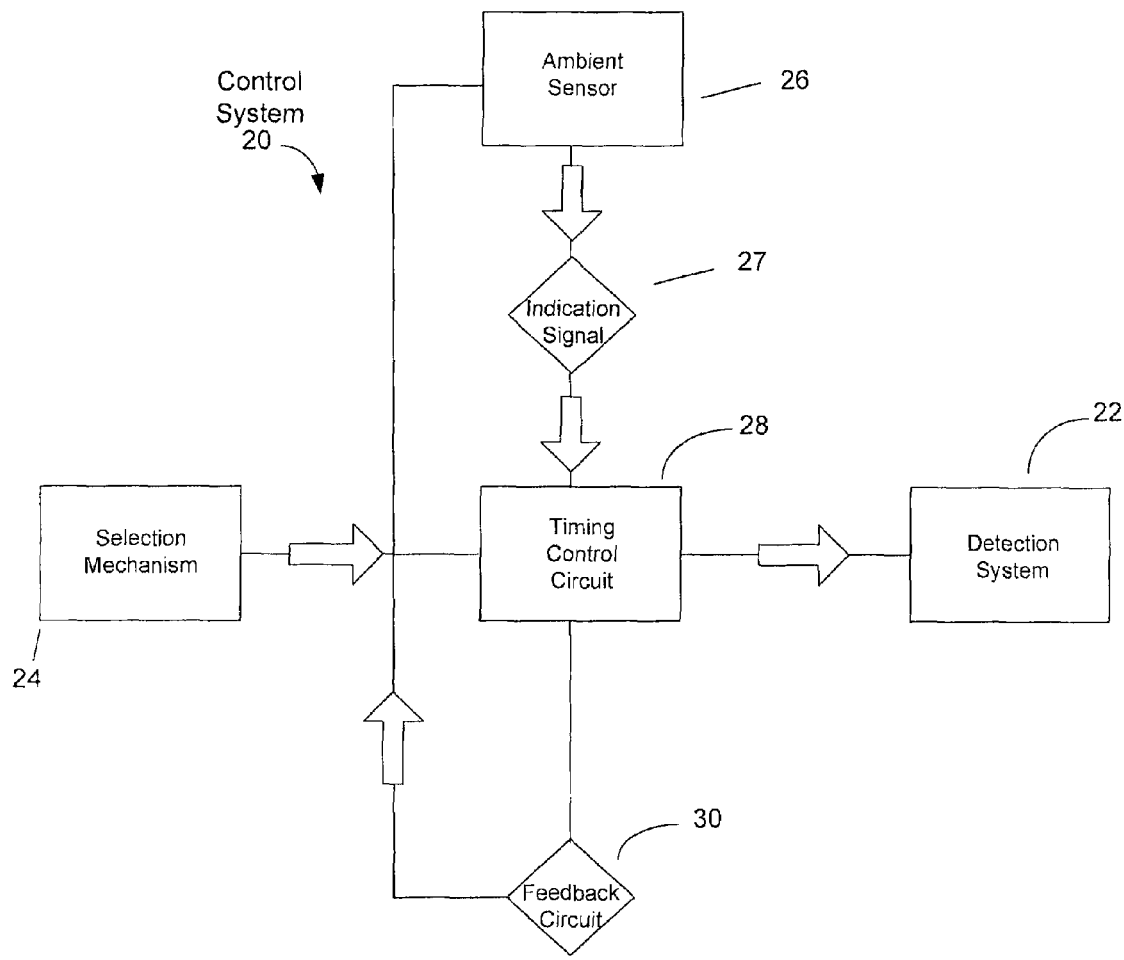
FIG. 2 shows a block diagram of a control system and method of use of the air treatment device.

Referring now to an exemplary embodiment of the interplay between FIGS. 2 and 3, the operation of the delivery mechanism 12 will be discussed. Initially, upon activation of the timing control circuit 28 (or at any point during operation) the user sets the mode in which the air treatment device 10 will operate via the selection mechanism 24. The selection mechanism 24 determines whether the control system 20 is ambient sensor activated, time activated, or a combination thereof.

If the user selects ambient sensor activation via the selection mechanism 24, the ambient sensor 26 is activated. The ambient sensor 26 then monitors the environment for changes in or the presence or absence of one or more ambient conditions. As stated above, the ambient sensor 26 is capable of detecting motion, temperature, light, humidity, or other static or changing conditions. If a change in ambient condition is detected by the ambient sensor 26, the timing control circuit 28 then activates the detection system 22 at specific time intervals and/or for a specific duration.

If the user selects timed activation via the selection mechanism 24, the selection mechanism 24 communicates with the timing control circuit 28. The timing control circuit 28 then activates the detection system 22 at specific time intervals and/or for a specific duration.

Once the detection system 22 is activated by the control system 20, the sensor 34 samples the environment for either the level of active air treatment material or the environment quality. The level of active air treatment material is sampled by the sensor 34 so as to maintain the desired level of active air treatment material. The environment quality is sampled by the sensor 34 so that in response to a decrease in the desired environment quality, the quantity of air treatment material dispensed may be increased.

If the predetermined level of environment quality is not met, e.g. the sensor 34 detects a malodor, the sensor 34 communicates with the activation circuit 36 to provide an increase in the quantity of air treatment material dispensed. Specifically, if the sensor 34 detects a malodor, it sends an indicator signal 37 to the activation circuit 36. The activation circuit 36 then activates the delivery system 38 accordingly. This action continues until the sensor 34 either determines the environment quality has returned to the predetermined level or the activation circuit 36 has triggered the dispersion of sufficient air treatment material.

Still further, in an exemplary embodiment, if the activation circuit 36 has triggered the dispersion of sufficient air treatment material, the activation circuit 36 disengages the sensor 34 for an operational time period via the feedback circuit 40. In exemplary embodiments, after the time period, the sensor 34, and thus the detection system 22, either is reengaged or remains disengaged until reengaged by the control system 20.

System for Active Treatment

Figure 4:
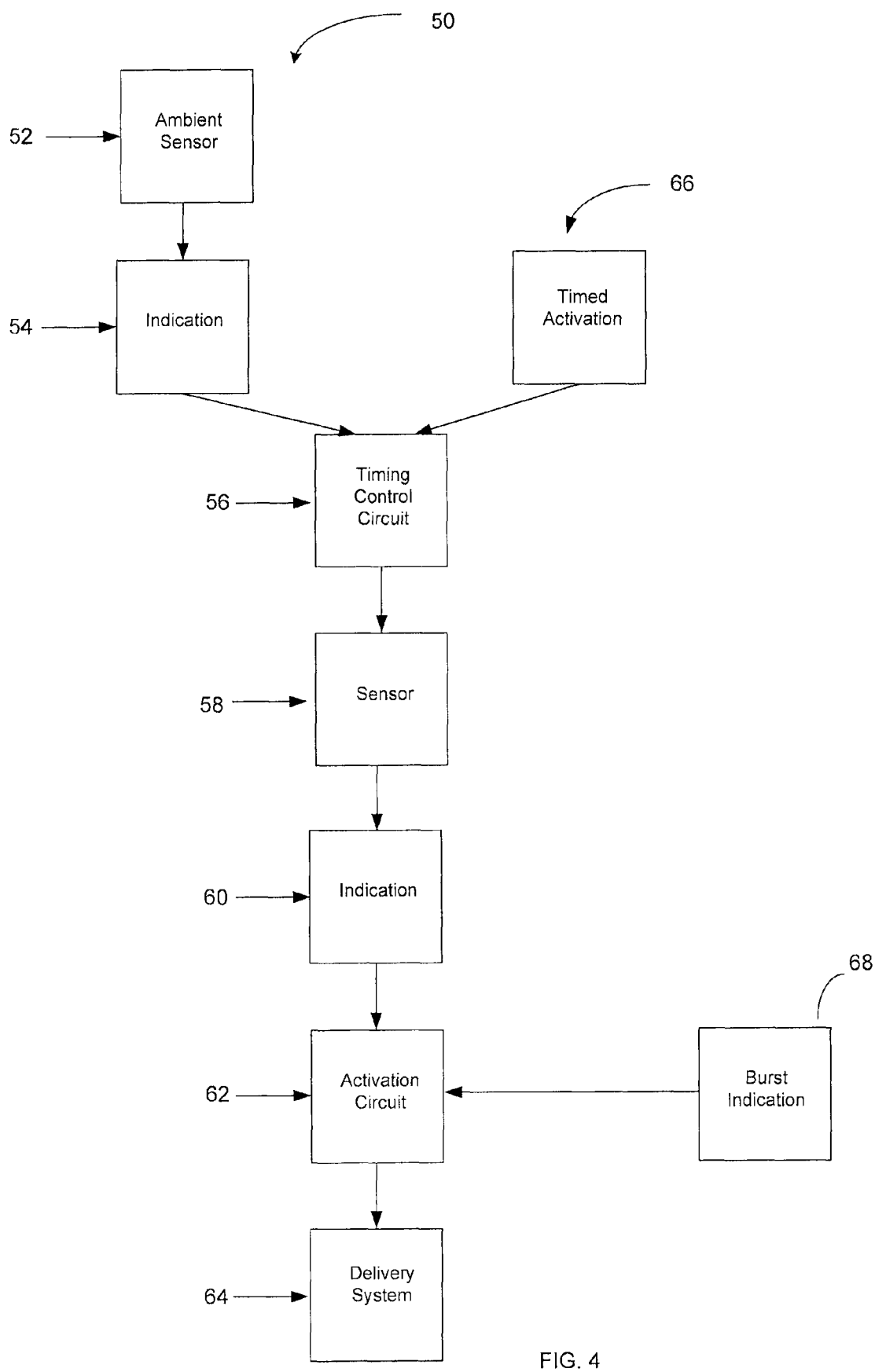
FIG. 4 shows a block diagram a system for dispensing air treatment.

FIG. 4 is a block diagram of a system 50 for active dispensing of an air treatment material, according to an exemplary embodiment. The system 50 is configured to dispense the air treatment material in three different manners.

The first manner in which the system 50 is configured to dispense the air treatment material comprises an ambient sensor 52 sensing a change in, or the presence or absence of, an ambient condition and sending an indication 54 to a timing control circuit 56. The timing control circuit 56 then sends an indication to activate a sensor 58 at a specific time interval and/or for a specific duration. Upon the sensor 58 detecting either a decreased level of active air treatment material or the presence of a malodor, an indication 60 is sent to an activation circuit 62. The activation circuit 62 then sends an indication to a delivery system 64 to dispense a volatizable liquid and/or fragrance.

The second manner in which the system 50 is configured to dispense the air treatment material comprises a timed activation 66. The timed activation 66 may be set by a user (e.g., the selection mechanism discussed infra), which would send an indication to the timing control circuit 56. The timing control circuit 56 then sends an indication to activate the sensor 58 at a specific time interval and/or for a specific duration. Upon the sensor 58 detecting either a decreased level of active air treatment material or the presence of a malodor, an indication 60 is sent to the activation circuit 62. The activation circuit 62 then sends an indication to the delivery system 64 to dispense a volatizable liquid and/or fragrance.

The third and final manner in which the system 50 is configured to dispense the air treatment material comprises a burst indication 68. The burst indication 68 may be the actuator 44 (shown in FIG. 1). Burst indication 68 is sent to an activation circuit 62. The activation circuit 62 then sends an indication to the delivery system 64 to dispense a volatizable liquid and/or fragrance.

The delivery system 64 may comprise an atomizer, spritzer, sprayer, pump, nozzle, or any other suitable dispenser for rapidly deploying an air treatment material within an area. The system 50 may include a multi-position switch to indicate which mode in which to operate.

Method for Active Treatment

Figure 5:
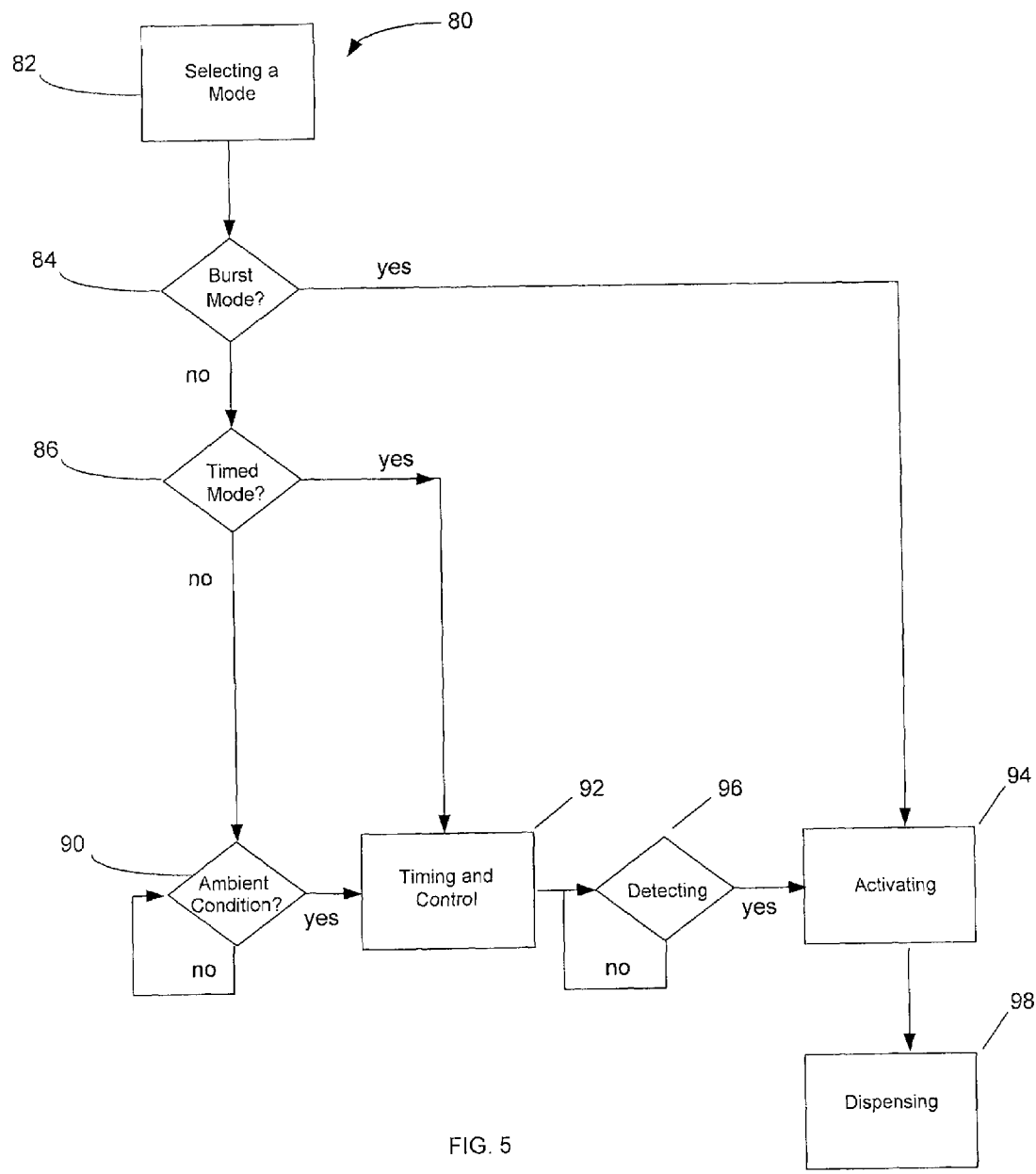
FIG. 5 shows a flow diagram of a method of dispensing air treatment.

FIG. 5 shows a flow diagram of a method 80 for active dispensing of an air treatment material, according to an exemplary embodiment. In this embodiment, the method 80 includes selecting a mode 82, determining if it is a burst mode 84, determining if it is a timed mode 86, detecting a change in, or the presence or absence of, an ambient condition 90, performing timing and control 92, detecting either a decreased level of active air treatment material or the presence of a malodor 96, activating 94, and dispensing 98.

In accordance with an exemplary embodiment, selecting the mode 82 includes selecting the mode of operation of the air treatment device. This may be done manually by a user, and/or may be generally automatic. The air treatment device may have any number of modes, from one to hundreds or more. In the embodiment shown in FIG. 5, there are three modes.

After the step of selecting the mode 82, a determination 84 is made if the device is in the burst mode. If the device is in the burst mode, the YES leg is taken to the activating step 94, which then, relatively immediately, dispenses the air treatment material at the dispensing step 98. The burst mode may or may not reset a timing control circuit and/or deactivate a sensor for a time period, depending on the method of delivery. If the device is not in the burst mode, the NO leg is taken.

If it is determined at step 86 the device is in the timed mode, the YES leg is taken to the timing and control step 92 upon which a sensor is activated at a specific time interval and/or for a specific duration. When the sensor detects either a decreased level of active air treatment material or the presence of a malodor at step 96, an indication signal is sent to the activating step 94, which then, relatively immediately, dispenses the air treatment material at the dispensing step 98. If the device is not in the timed mode, the NO leg is taken.

At step 90, an ambient sensor detects a change in, or the presence or absence of, an ambient condition. If detected, the YES leg is taken to the timing and control step 92 upon which a sensor is activated at a specific time interval and/or for a specific duration. When the sensor detects either a decreased level of active air treatment material or the presence of a malodor at step 96, an indication signal is sent to the activating step 94, which then, relatively immediately, dispenses the air treatment material at the dispensing step 98. If not detected, the NO leg is taken.

As used herein, the terms "comprise", "comprises", "comprising", "having", "including", "includes", or any variation thereof, are intended to reference a non-exclusive inclusion, such that a process, method, article, composition or apparatus that comprises a list of elements does not include only those elements recited, but can also include other elements not expressly listed and equivalents inherently known or obvious to those of reasonable skill in the art. Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters or other operating requirements without departing from the scope of the instant invention and are intended to be included in this disclosure.

Moreover, unless specifically noted, it is the Applicant's intent that the words and phrases in the specification and the claims be given the commonly accepted generic meaning or an ordinary and accustomed meaning used by those of reasonable skill in the applicable arts. In the instance where these meanings differ, the words and phrases in the specification and the claims should be given the broadest possible, generic meaning. If it is intended to limit or narrow these meanings, specific, descriptive adjectives will be used. Absent the use of these specific adjectives, the words and phrases in the specification and the claims should be given the broadest possible meaning. If any other special meaning is intended for any word or phrase, the specification will clearly state and define the special meaning.

It should be understood that the foregoing description is of exemplary embodiments of the invention only, and that the invention is not limited to the specific forms shown. Various modifications may be made in the design and arrangement of the elements set forth herein without departing from the scope of the invention.

What is claimed is:

1. An air treatment method, comprising the steps of:
providing an air treatment material;
providing a malodor detection system;
adjusting the responsiveness of said malodor detection system;
periodically activating and deactivating said malodor detection system at a specific time interval in response to a change in, or the presence or absence of, an ambient condition;
detecting either a decreased level of said air treatment material or the presence of a malodor; and
dispensing said air treatment material in response to said decreased level of said air treatment material or said malodor.

2. The air treatment system of claim 1, wherein said ambient condition comprises one or more of motion, temperature, light and humidity.

3. The air treatment system of claim 1, wherein said step of periodically activating and deactivating said malodor detection system further comprises periodically activating and deactivating said malodor detection system at a specific time interval and/or for a specific duration.

* * * * *